United States Patent [19]

Nobusawa et al.

[11] Patent Number: 5,276,234
[45] Date of Patent: Jan. 4, 1994

[54] PROCESS FOR PRODUCING 2-METHYLNAPHTHALENE

[75] Inventors: Tatsuya Nobusawa; Toshihide Suzuki; Akinori Matsuura, all of Chiba, Japan

[73] Assignee: Kawasaki Steel Corporation, Japan

[21] Appl. No.: 757,224

[22] Filed: Sep. 10, 1991

[30] Foreign Application Priority Data

Sep. 13, 1990 [JP] Japan .................. 2-243050

[51] Int. Cl.$^5$ .................. C07C 5/367; C07C 15/16
[52] U.S. Cl. .................. 585/430; 585/400; 585/440; 585/481; 585/482
[58] Field of Search ............... 585/481, 482, 400, 430, 585/440

[56] References Cited

U.S. PATENT DOCUMENTS 3,887,630 6/1975 Ward .................. 585/482

Primary Examiner—Patrick P. Garvin
Assistant Examiner—Brent M. Peebles
Attorney, Agent, or Firm—Bierman and Muserlian

[57] ABSTRACT

The invention provides a process for producing 2-methylnaphthalene by isomerization of 1-methylnaphthalene in which a Y zeolite having a unit cell constant of less than or equal to 24.37 Å ($10^{-10}$ m) is used as an isomerization catalyst.

Since the isomerization is effected by the use of the inventive heterogeneous solid catalyst which has a long catalyst life, 2-methylnaphthalene is produced from 1-methylnaphthalene efficiently with less cost and handling steps for regeneration or exchange of the catalyst.

5 Claims, 1 Drawing Sheet

PROCESS FOR PRODUCING 2-METHYLNAPHTHALENE

FIELD OF THE INVENTION

This invention relates to a process for the production of 2-methylnaphthalene from 1-methylnaphthalene by its isomerization reaction.

BACKGROUND OF THE INVENTION

2-Methylnaphthalene is a useful compound as an intermediate material for the synthesis of dyes, medicines and the like. Also, this compound has recently been drawing attention as an intermediate material for the synthesis of 2,6-naphthalenedicarboxylic acid which is a monomer of highly functional resins.

Since 2-methylnaphthalene is contained in a methylnaphthalene cut or fraction which is obtained by distillation of tar resulting from carbonization of coal, this compound has been produced in the prior art processes by recovering it from such a methylnaphthalene fraction by means of crystallization or distillation after extracting and removing basic materials. The methylnaphthalene fraction freed from basic materials for use in the crystallization or distillation contains not only 2-methylnaphthalene but also a large quantity of 1-methylnaphthalene which, as a matter of course, remains in a large amount in a recovery solution after crystallization or distillation of 2-methylnaphthalene. Though 1-methylnaphthalene finds some use in such applications as dyes and the like, its demands for industrial use are not high in comparison with the case of 2-methylnaphthalene. In consequence, several processes for the efficient production of 2-methylnaphthalene have been proposed in which 1-methylnaphthalene remained in a recovery solution after crystallization or distillation of 2-methylnaphthalene, or contained in a starting material before the recovery process, is isomerized into 2-methylnaphthalene.

It is known that isomerization of alkylaromatics is promoted by acid catalysts including homogeneous acid catalysts such as $AlCl_3$, $HF-BF_3$ and the like and heterogeneous counterparts such as silica alumina, zeolites, modified zeolites and the like. As an example of the application of a homogeneous acid catalyst, Japanese Patent Publication No. Hei 01-13454 discloses a process in which selectivity of 2-methylnaphthalene is improved by using $BF_3-H_3PO_4$. As to the application of heterogeneous acid catalysts, improvement of 2-methylnaphthalene selectivity by the use of partially ion-exchanged Y zeolites has been reported by V. Solinas et al. (*Applied Catalysis*, vol. 9, pp. 109-117, 1984).

In the prior art processes, isomerization of 1-methylnaphthalene has been carried out making use of these acid catalysts, but with some disadvantages.

For instance, when the aforementioned $BF_3-H_3PO_4$ is used as a homogeneous acid catalyst, its handling is attended with possible danger of inflicting drug injury or toxication. In addition, though $H_3PO_4$ in this catalyst can be used again, the expensive $BF_3$ portion is dissolved in the product and decomposed by water. In consequence, utilization of such a homogeneous acid catalyst has disadvantages in that not only the catalyst itself is dangerous to handle but also its recovery is not easy.

On the other hand, as described in the foregoing, isomerization of 1-methylnaphthalene into 2-methylnaphthalene can be effected making use of heterogeneous acid catalysts such as silica alumina, zeolites, modified zeolites and the like. For example, deterioration with age in the activity of partially ion-exchanged Y zeolites are described in the aforementioned reference by Solinas et al. According to the results of their experiments, however, the isomerization process could not be applied to industrial production of 2-methylnaphthalene because of too quick deterioration of the catalyst. As can be understood from the just described example, isomerization of 1-methylnaphthalene making use of a solid and acidic heterogeneous catalyst has a problem of quick decrease in the catalytic activity because of markedly rapid deterioration of the catalyst due to the deposition of carbonaceous materials.

Because of these problems involved in the prior art processes for the production of 2-methylnaphthalene by isomerization of 1-methylnaphthalene, development of a process in which a heterogeneous catalyst that can be handled and recovered easily and has a long catalyst life is used has been called for in the related industrial field.

SUMMARY OF THE INVENTION

In view of the above, it therefore becomes an object of the present invention to provide a process for the production of 2-methylnaphthalene from 1-methylnaphthalene by its isomerization making use of a heterogeneous catalyst having an extended catalyst life.

Particularly, in accordance with the present invention, there is provided a process for producing 2-methylnaphthalene by isomerization of 1-methylnaphthalene which comprises using a Y zeolite having a unit cell constant of less than or equal to 24.37 Å ($10^{-10}$ m) as an isomerization catalyst and carrying out the isomerization reaction at a temperature in the range of from 350° to 600° C. Preferably, the Y zeolite having a unit cell constant of less than or equal to 24.37 Å is a Y zeolite resulting from adjustment of its unit cell constant to 24.37 Å or less by a steam treatment at a temperature in the range of from 400° to 1000° C. and/or an acid treatment.

Another object of the present invention is to provide a process for producing 2-methylnaphthalene by isomerization of 1-methylnaphthalene which comprises using a Y zeolite resulting from a steam treatment and/or an acid treatment as an isomerization catalyst and carrying out the isomerization reaction at a temperature in the range of from 350° to 600° C.

Still another object of the present invention is to provide a catalyst for use in isomerization of 1-methylnaphthalene into 2-methylnaphthalene which comprises a Y zeolite having a unit cell constant of less than or equal to 24.37 Å ($10^{-10}$ m).

Other objects and advantages of the present invention will be made apparent as the description progresses.

DETAILED DESCRIPTION OF THE INVENTION

Figure 1:
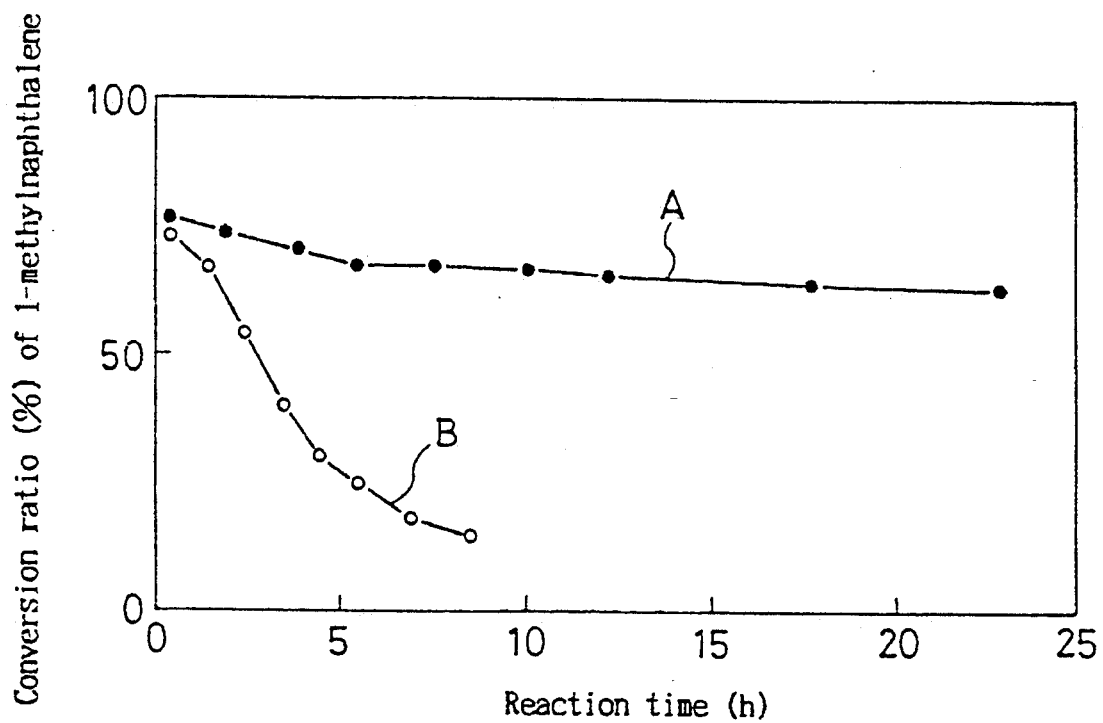
FIG. 1 is a graph showing periodical changes in the conversion ratio of 1-methylnaphthalene in the case of Example 1 (A) and Comparative Example 1 (B).

With the aim of overcoming the aforementioned problems involved in the prior art, the inventors of the present invention have examined various Y zeolites having different $SiO_2/Al_2O_3$ ratios as catalysts for use in 1-methylnaphthalene to 2-methylnaphthalene isomerization and found that durability of catalytic activity of Y zeolites increased as their $SiO_2/Al_2O_3$ ratios increased. Thereafter, the present inventors have further studied on the optimum $SiO_2/Al_2O_3$ ratio of Y zeolite as well as its optimum isomerization reaction temperature. As the results, it was found that a Y zeolite can exhibit markedly prolonged durability of its catalytic activity in isomerizing 1-methylnaphthalene at a temperature of from 350° to 600° C. when unit cell constant of the zeolite is reduced to a level of 24.37 Å or below by means of dealumination. The present invention has been accomplished as a result of these efforts.

Consequently, in accordance with the present invention, there is provided a process for producing 2-methylnaphthalene by isomerization of 1-methylnaphthalene which comprises using a Y zeolite having a unit cell constant of less than or equal to 24.37 Å ($10^{-10}$ m) as an isomerization catalyst and carrying out the isomerization reaction at a temperature in the range of from 350° to 600° C.

In this instance, compositions of Y zeolites to be used ($SiO_2/Al_2O_3$ ratios) are defined by unit cell constants, because unit cell constants of Y zeolites generally become small as decreasing the contents of aluminum in a framework constituting elements and therefore the unit cell constant can be used as an index of the framework constituting aluminium contents. Relationship between unit cell constants and contents of aluminium which constitutes framework of Y zeolites is described for example in *Crystal Research and Technology* (H. Fichtner-Schmittler et al., 19, 1984, 1, K1-K3).

The following describes the present invention in detail.

In the production process of the present invention, 1-methylnaphthalene is used as the starting material for isomerization reaction. Purity of this starting material is not so important and it therefore may contain 2-methylnaphthalene in a level lower than its equilibrium concentration, [2-methylnaphthalene/(1 and 2-methylnaphthalene)]=65 mol %. Also, the starting material may contain incidental impurities such as naphthalene.

Illustrative examples of the starting material include 1-methylnaphthalene containing oil materials such as coal tar fractions, petroleum fractions and the like, more particularly, a methylnaphthalene fraction containing 1-methylnaphthalene and 2-methylnaphthalene from which basic materials have been removed, and a residual liquid obtained after recovery of 2-methylnaphthalene from such a methylnaphthalene fraction by means of crystallization or distillation.

From an industrial production point of view, the 1-methylnaphthalene-containing oil to be used as the starting material may contain 1-methylnaphthalene preferably in an amount of at least 10% by weight, more preferably 20% by weight or more.

The catalyst to be used in the present invention is a Y zeolite having a unit cell constant of 24.37 Å or less.

As described in the foregoing, unit cell constant of a Y zeolite represents composition of its framework constructing elements. According to the aforementioned reference (*Crystal Research and Technology*, vol. 19, 1984), when degree of dealumination (a process for the removal of aluminium from unit cells) of a Y zeolite is increased, the unit cell constant extrapolated to 0% aluminium content becomes 24.2 Å ($10^{-10}$ m), indicating that a Y zeolite having a unit cell constant of less than 24.2 Å does not exist in theory. In other words, the Y zeolite to be used in the present invention having a unit cell constant of less than or equal to 24.37 Å can be regarded as a Y zeolite having extremely large $SiO_2/Al_2O_3$ ratio which is attained by exhaustive dealumination.

Any of Y zeolites having different $SiO_2/Al_2O_3$ ratios may be used as the starting material of the Y zeolite of the present invention having a unit cell constant of less than or equal to 24.37 Å, but commercially available USY (ultrastabilized Y type) zeolites in which $SiO_2/Al_2O_3$ ratios have already been increased may be used preferably because further dealumination can be made smoothly.

A Y zeolite to be subjected to dealumination should be the one in which entire, most or a part of its cationic sites have been exchanged by protons or ammonium ions.

For the purpose of reducing unit cell constant of a starting Y zeolite material to a level of 24.37 Å or below, the zeolite may be subjected to dealumination by means of a steam treatment and/or an acid treatment.

Such a steam treatment may be carried out in steam or in a mixed atmosphere of steam and other gas such as air, nitrogen and the like.

The steam treatment may be carried out at a temperature of from 400° to 1000° C., preferably from 500° to 800° C. The treatment temperature if too low would bear no significant dealumination effect and therefore no effect on the reduction of unit cell constants, while too high temperatures would cause destruction of zeolite crystals and therefore would result in the reduction of crystallinity and catalytic activity. In addition, dealumination by steam treatment at too high temperatures is disadvantageous from economical point of view because such a treatment requires a reaction vessel having high heat and corrosion resistances.

Generally, an acid treatment is carried out after the steam treatment in order to remove aluminium which has been freed from the crystal lattice by the steam treatment. In the process of the present invention, the acid treatment may be carried out alone or after the steam treatment or may not be employed when sufficient dealumination is attained by the steam treatment.

The acid treatment can be effected for instance by using a mineral acid such as HCl, $H_2SO_4$, $HNO_3$ or the like. For example, when dealumination treatment is carried out using HCl, the treatment may be completed simply by suspending and stirring a Y zeolite of interest in an aqueous solution of 0.1 to 5N HCl. In this instance, concentration of HCl if too low would bear no significant dealumination effect and too high a concentration would reduce crystallinity of Y zeolite and therefore its catalytic activity. In addition, dealumination by acid treatment at too high HCl concentration is disadvantageous from economical point of view because such a treatment requires a reaction vessel having high corrosion resistance.

When aluminium is removed from the crystal lattice of a Y zeolite by subjecting the zeolite to a steam treatment and/or an acid treatment in this manner, the resulting dealuminated zeolite shows an extended catalyst life. Though the reason for such an effect is not clear, it seems that the morphology of a Y zeolite is changed by the dealumination into such a form that the catalytic activity hardly decreases when carbonaceous materials are deposited, or that acidic nature of the zeolite is changed by the dealumination in such a manner that deposition of carbonaceous materials is repressed when the dealuminated zeolite is used as a catalyst.

By these dealumination treatments, a Y zeolite having a unit cell constant of less than or equal to 24.37 Å is obtained. When unit cell constant of the Y zeolite exceeds 24.37 Å, it will show a short durability in terms of its catalytic activity to isomerize 1-methylnaphthalene. On the other hand, larger $SiO_2/Al_2O_3$ ratio or smaller unit cell constant of the dealuminated Y zeolite is accompanied by a corresponding increase in its durability in terms of its catalytic activity to isomerize 1-methylnaphthalene. Too much dealumination by a steaming and/or an acid treatment, however, will cause destruction of crystals, reduction of active sites and the like, thus bringing up a problem of lowered level of catalytic activity in spite of high durability of the activity. In such an instance, a high conversion ratio with an extended durability may be achieved for example by reducing flow rate of the feedstock, 1-methylnaphthalene, per unit weight of the catalyst when the isomerization reaction is carried out. For the purpose of attaining high catalytic activity and extended durability at the same time, a Y zeolite to be used may have a unit cell constant of less than or equal to 24.37 Å, preferably in the range of from 24.27 to 24.35 Å, more preferably from 24.28 to 24.34 Å.

Though the Y zeolite to be used in the process of the present invention has a unit cell constant of less than or equal to 24.37 Å, other Y zeolites having unit cell constants of more than 24.37 Å may be contained provided that they do not spoil the effects of the present invention.

When a catalyst containing a Y zeolite prepared for other purposes such as an fluidized catalytic cracking process and whose unit cell constant is reduced to less than 24.37 Å through the heat treatment in an fluidized catalytic cracking reactor or a regenerator is used in the isomerization of 1-methylnaphthalene, it can achieve high durability of catalytic activity.

As has been described in the foregoing, according to the present invention, 2-methylnaphthalene is produced by isomerizing 1-methylnaphthalene in the presence of the thus prepared Y zeolite having a unit cell constant of less than or equal to 24.37 Å. In this instance, the isomerization reaction may be carried out at a temperature of from 350° to 600° C., preferably from 400° to 500° C., more preferably from 420° to 480° C.

It has been revealed through studies by the present inventors that a highly dealuminated Y zeolite has a low temperature active site which shows 1-methylnaphthalene isomerization activity at a low temperature but is quickly inactivated and a high temperature active site which shows its activity only at a high temperature but is possessed of an extended durability. When isomerization of 1-methylnaphthalene is carried out using such a catalyst at a temperature of less than 350° C., the low temperature active site is inactivated within a short time at early stage of the reaction thus leaving only the high temperature active site-related activity, but a satisfactory conversion ratio cannot be obtained by the activity of the remaining high temperature active site because of its low reaction rate at such a low temperature. When the reaction temperature is controlled within the preferred range, a satisfactorily high conversion ratio can be obtained by the action of the high temperature active site even after early stage inactivation of the catalytic activity of the low temperature active site. Too high a reaction temperature (exceeding 600° C.), however, will accelerate deterioration of the catalyst due to increase in the formation rate of carbonaceous deposits. Also, such a exceedingly high reaction temperature is not preferably because of the generation of side reactions which result in the formation of by-products such as naphthalene, dimethylnaphthalene and the like.

In accordance with the production process of the present invention, both flow and batch systems are applicable to the isomerization of 1-methylnaphthalene, but flow system may be more suitable than batch system from industrial production and economical points of view.

The isomerization reaction may be carried out in either a gas phase or a liquid phase.

In the case of a liquid phase reaction, extended catalyst life will be obtained because precursors of carbonaceous materials deposited on the catalyst surface are removable by dissolving them in the liquid medium. Contrary to this, however, it is necessary to pressurize the reaction system to maintain its liquid state when the reaction is carried out at a temperature equal to or higher than the boiling point of 1-methylnaphthalene (245° C.), thus resulting in the necessity of pressure proof facilities and in the increment of power cost.

In the case of a gas phase reaction, it has advantages in that pressure proof facilities are not required and power cost is reduced, because the isomerization reaction can be carried out at atmospheric pressure or under a slightly pressurized condition. However, the gas phase reaction also has disadvantages such as rapid deterioration of catalyst due to deposition of carbonaceous materials and, in some cases, additional cost for dilution gas. In the gas phase reaction, though not always required, a dilution gas such as nitrogen, steam, hydrogen or the like may be used, preferably hydrogen for the purpose of improving durability of catalytic activity.

According to the production process of the present invention, WHSV (weight of 1-methylnaphthalene passing through unit weight of catalyst in 1 hour) may preferably be in the range of from 0.1 to 10 $h^{-1}$. The WHSV if too large would bear insufficient conversion ratio, which too small WHSV would require a large amount of packed catalyst and a large volume reactor which are uneconomical.

Thus, 2-methylnaphthalene is produced through isomerization of 1-methylnaphthalene in the aforementioned manner. In this instance, used catalyst can be regenerated for example by baking deteriorated catalyst due to deposition of carbonaceous materials from the reaction system at a temperature of about 300° to about 800° C. in the air or in an oxygen atmosphere.

In addition, decrease in the catalytic activity can be delayed by loading the catalyst for example with the group VIII metal ions in the periodic table such as Fe, Co, Ni, Pd, Pt and the like by ion exchanging and the like means.

EXAMPLES

The following inventive and comparative examples are provided to further illustrate the present invention, but not by way of limitation.

Unit cell constants of zeolites as described in the following examples were measured by XRD (X-ray diffraction) under the following conditions and calculated from the peak position of (5 3 3) plane.

Target/filter: Co/Fe
Voltage/current: 50 kV/30 mA
Irradiation side slit: 1.0 DEG
Scatter slit: 1.0 DEG X-ray receiving side slit: 0.3 mm
Measuring resolution: 0.02 DEG
Preset time: 0.4 second
Detector: scintillation counter
X-ray diffractometer: RAD-IIA by Rigaku Denki Kogyo Co., Ltd.

EXAMPLE 1

A stainless steel reaction tube was packed with 5 g of a Y zeolite (unit cell constant, 24.63 Å) having $SiO_2/Al_2O_3$ (molar ratio)=4.9 in which the cation site has been exchanged by protons, and the packed zeolite was treated at 600° C. for 6 hours in an atmosphere of 100% steam. Charged water during this treatment was 200 ml. Unit cell constant of the thus treated Y zeolite was measured to be 24.28 Å.

Using a stainless steel reaction tube packed with 0.5 g of the thus treated Y zeolite, isomerization of 1-methylnaphthalene was carried out at 450° C. under atmospheric pressure, with flow rates of 20 N.T.P. (normal temperature and pressure) ml/min of hydrogen and 0.75 g/hr of 1-methylnaphthalene. Conversion ratio of 1-methylnaphthalene was measured at intervals, with the results shown as line A in FIG. 1. In this experiment, changes in the selectivity of 2-methylnaphthalene were almost constant (about 90%) through the reaction period.

COMPARATIVE EXAMPLE 1

Isomerization of 1-methylnaphthalene was carried out in the same manner as the process in Example 1 except that the Y zeolite used in Example 1 was not subjected to steam treatment (unit cell constant, 24.63 Å). Conversion ratio of 1-methylnaphthalene was measured at intervals, with the results shown as line B in FIG. 1. In this experiment, changes in the selectivity of converted 1-methylnaphthalene to 2-methylnaphthalene were almost constant (about 90%) through the reaction period.

EXAMPLE 2

Steam treatment of Y zeolite and isomerization of 1-methylnaphthalene were carried out in the same manner as the process in Example 1 except that a Y zeolite, ZCP-50 (unit cell constant 24.65 Å, manufactured by Catalysts & Chemicals Industries Co., Ltd.), whose cationic site has been ion-ecxchanged by protons was used as the starting zeolite. Unit cell constant of the steam-treated Y zeolite was measured to be 24.30 Å. Conversion ratio of 1-methylnaphthalene and yield of 2-methylnaphthalene were measured at intervals, with the results shown in Table 1.

COMPARATIVE EXAMPLE 2

Isomerization of 1-methylnaphthalene was carried out in the same manner as the process in Example 2 except that the Y zeolite used in Example 2 was not subjected to steam treatment. Conversion ratio of 1-methylnaphthalene and yield of 2-methylnaphthalene were measured at intervals, with the results shown in Table 1.

EXAMPLE 3

Steam treated zeolite (unit cell constant, 24.36 Å) whose cationic site has been ion-ecxchanged by protons was used as the starting zeolite. Then the starting zeolite was steam treated again in the same manner in Example 1. Isomerization of 1-methylnaphthalene were carried out in the same manner as the process in Example 1. Unit cell constant of the twice steam-treated Y zeolite was measured to be 24.29 Å. Conversion ratio of 1-methylnaphthalene and yield of 2-methylnaphthalene were measured at intervals, with the results shown in Table 1.

COMPARATIVE EXAMPLE 3

Isomerization of 1-methylnaphthalene was carried out in the same manner as the process in Example 3 except that the Y zeolite used in Example 3 was not subjected to the second steam treatment. The unit cell constant of the Y zeolite used in this experiment was 24.38 Å. Conversion ratio of 1-methylnaphthalene and yield of 2-methylnaphthalene were measured at intervals, with the results shown in Table 1.

EXAMPLE 4

Isomerization of 1-methlnaphthalene was carried out in the same manner as the process in Example 1 except that the steam treated Y zeolite having the unit cell constant of 24.34 Å. Conversion ratio of 1-methylnaphthalene and yield of 2-methylnaphthalene were measured at intervals, with the results shown in Table 1.

EXAMPLE 5

Isomerization of 1-methylnaphthalene was carried out in the same manner as the process in Example 3 except that the reaction temperature was changed to 410° C. Conversion ratio of 1-methylnaphthalene and yield of 2-methylnaphthalene were measured at intervals, with the results shown in Table 1.

EXAMPLE 6

Isomerization of 1-methylnaphthalene was carried out in the same manner as the process in Example 3 except that the reaction temperature was changed to 490° C. Conversion ratio of 1-methylnaphthalene and yield of 2-methylnaphthalene were measured at intervalÅ, with the results shown in Table 1.

EXAMPLE 7

A stainless steel reaction tube was packed with 2 g of a catalyst (unit cell constant 24.29 Å) which has been prepared from the same starting Y zeolite as used in Example 3 by the same steam treatment as in Example 3. Using the thus packed catalyst, liquid phase isomerization of 1-methylnaphthalene was carried out at 450° C. under a pressure of 50 kg/cm² G, with a 1-methylnaphthalene supply rate of 3 g/hr in the absence of dilution gas. Conversion ratio of 1-methylnaphthalene and yield of 2-methylnaphthalene were measured at intervals, with the results shown in Table 1.

COMPARATIVE EXAMPLE 4

Isomerization of 1-methylnaphthalene was carried out in the same manner as the process in Example 7 except that the same Y zeolite used in example 1 was not subjected to steam treatment and has a unit cell constant of 24.63 Å. Conversion ratio of 1-methylnaphthalene and yield of 2-methylnaphthalene were measured at intervals, with the results shown in Table 1.

TABLE 1

|  | Inventive Example | | | | | | Comparative Example | | |
| --- | --- | --- | --- | --- | --- | --- | --- | --- | --- |
|  | 2 A/B | 3 A/B | 4 A/B | 5 A/B | 6 A/B | 7* A/B | 2 A/B | 3 A/B | 4* A/B |
| Unit cell const. of Y zeolite (Å) | 24.30 | 24.29 | 24.34 | 24.29 | 24.29 | 24.29 | 24.65 | 24.38 | 24.63 |
| Isomerization temperature (°C.) | 450 | 450 | 450 | 410 | 490 | 450 | 450 | 450 | 450 |
| Reaction time (hr) | | | | | | | | | |
| 5 | 71/55 | 71/55 | 71/55 | 48/40 | 72/51 | 78/45 | 25/22 | 65/60 | 45/30 |
| 10 | 68/56 | 70/56 | 68/56 | 38/33 | 68/51 | 75/48 | 12/11 | 54/49 | 25/16 |
| 20 | 67/56 | 68/56 | 65/55 | 36/30 | 60/51 | 72/50 |  | 38/35 | 9/6 |
| 50 | 60/53 | 60/53 | 57/50 | 32/29 | 40/36 | 68/51 |  | 20/17 |  |
| 100 | 51/48 | 50/47 | 43/40 |  |  | 52/45 |  |  |  |

Note: A, conversion ratio of 1-methylnaphthalene
B, yield of 2-methylnaphthalene
*liquid phase isomerization The following is obvious from Table 1.

When a Y zeolite having a unit cell constant of less than or equal to 24.37 Å is used, the durability of catalytic activity is definitely longer than when a Y zeolite having a unit cell constant of more than 24.37 Å is used (comparison between Inventive Examples 2 and 4, and Comparative Example 2, between Inventive Example 3 and Comparative Example 3 and between Inventive Example 7 and Comparative Example 4).

In addition, the most preferrable reaction temperature for the isomerization of 1-methylnaphthalene into 2-methylnaphthalene is around 450° C. (as shown in Inventive Example 3). When the reaction temperature is higher (Inventive Example 6) or lower (Inventive Example 5) than the level, the reactivity is lowered.

For comparison of data between Inventive Example 5 and Comparative Example 3, when the reaction time is 5 hours and 10 hours, the conversion ratio of 1-methylnaphthalene and yield of 2-methylnaphthalene of Comparative Example 3 are higher than those of Inventive Example 5. This is because the reaction temperature of Comparative Example 3 is higher than that of Inventive Example 5. However, when the reaction time is more than 20 hours, the conversion ratio of 1-methylnaphthalene and yield of 2-methylnaphthalene of Inventive Example 5 are higher than those of Comparative Example 3. Therefore, it is evident that a Y zeolite used in the present invention is superior in the durability of catalytic activity.

High conversion ratio of 1-methylnaphthalene and high yield of 2-methylnaphthalene can be attained by the use of the inventive Y zeolite catalyst due to its long catalyst life. The present process is suitable for industrial scale production of 2-methylnaphthalene by isomerization of 1-methylnaphthalene.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A process for producing 2-methylnaphthalene by isomerization of 1-methylnaphthalene which comprises using a Y zeolite having a unit cell constant of less than or equal to 24.37 Å ($10^{-10}$ m) as an isomerization catalyst and carrying out the isomerization reaction at a temperature in the range of from 350° to 600° C.

2. A process for producing 2-methylnaphthalene by isomerization of 1-methylnaphthalene which comprises using a Y zeolite resulting from a steam treatment and/or an acid treatment as an isomerization catalyst and carrying out the isomerization reaction at a temperature in the range of from 350° to 600° C.

3. The process for producing 2-methylnaphthalene according to claim 1 wherein said Y zeolite having a unit cell constant of less than or equal to 24.37 Å is a Y zeolite resulting from adjustment of its unit cell constant to 24.37 Å or less by a steam treatment at a temperature in the range of from 400° to 1000° C. and/or an acid treatment.

4. The process acording to claim 1, wherein the Y zeolite has a unit cell constant of 24.27 to 24.35 Å.

5. The process according to claim 1, wherein the isomerization reation temperature is in the range of from 400° to 500° C.

* * * * *